(12) United States Patent
McNall, III et al.

(10) Patent No.: US 11,338,082 B2
(45) Date of Patent: May 24, 2022

(54) VARIABLE RATE DISPENSER WITH ASEPTIC SPIKE CONNECTOR ASSEMBLY

(71) Applicant: BioQ Pharma, Inc., San Francisco, CA (US)

(72) Inventors: Ralph I. McNall, III, Belmont, CA (US); Thomas T. Donze, San Bruno, CA (US); Andrew M. Godin, South San Francisco, CA (US); Serena Joshi, San Francisco, CA (US)

(73) Assignee: BloQ Pharma, Inc., San Francisco, CA (US)

( * ) Notice: Subject to any disclaimer, the term of this patent is extended or adjusted under 35 U.S.C. 154(b) by 320 days.

(21) Appl. No.: 16/560,929

(22) Filed: Sep. 4, 2019

(65) Prior Publication Data
US 2021/0060239 A1    Mar. 4, 2021

(51) Int. Cl.
  *A61M 5/142* (2006.01)
  *A61M 5/14* (2006.01)
  *A61M 5/168* (2006.01)
  *A61M 5/172* (2006.01)
  *A61M 39/16* (2006.01)
  *A61J 1/20* (2006.01)

(52) U.S. Cl.
  CPC ........ *A61M 5/14232* (2013.01); *A61J 1/2024* (2015.05); *A61M 5/1413* (2013.01); *A61M 5/16877* (2013.01); *A61M 5/172* (2013.01); *A61M 39/165* (2013.01); *A61J 1/201* (2015.05); *A61M 2205/3334* (2013.01); *A61M 2205/8206* (2013.01)

(58) Field of Classification Search
  CPC .. A61M 39/18; A61J 1/20; A61J 1/201; A61J 1/2051; A61J 1/2048; A61J 1/1046; A61J 1/1412; A61J 1/2024
  See application file for complete search history.

(56) References Cited

U.S. PATENT DOCUMENTS

| 3,727,463 | A |  | 4/1973 | Intraub |
| 3,909,910 | A |  | 10/1975 | Rowe et al. |
| 4,019,512 | A | * | 4/1977 | Tenczar ............... A61M 39/14 604/411 |

(Continued)

FOREIGN PATENT DOCUMENTS

| JP | S49129223 |  | 12/1974 |
| JP | S63230175 | A | 9/1988 |
| WO | 2011002853 | A2 | 1/2011 |

*Primary Examiner* — Laura A Bouchelle
(74) *Attorney, Agent, or Firm* — Thomas W. Galvani, P.C.; Thomas W. Galvani

(57) ABSTRACT

A dispenser includes a container with an endwall and a cap covering the endwall. The cap has an aperture and a first film covering the aperture. A hood over the cap has a barrel defining a bore which is coaxially aligned with the aperture, a second film sealing the bore, and a gasket compressed behind the second film. A spike is carried for movement in the barrel between retracted and advanced positions. The dispenser has first and second conditions. In the first condition, the first and second films are against each other and seal the aperture and barrel, and in the second condition, the first and second films are away, unsealing the aperture and the barrel. When the dispenser is in the second condition and the spike moves from the retracted position to the advanced position, the spike pierces the endwall.

34 Claims, 10 Drawing Sheets

(56) References Cited

U.S. PATENT DOCUMENTS

| | | |
|---|---|---|
| 4,137,913 A | 2/1979 | Georgi |
| 4,392,734 A | 7/1983 | Plumadore |
| 4,396,385 A | 8/1983 | Kelly et al. |
| 4,435,173 A | 3/1984 | Siposs et al. |
| 4,585,436 A | 4/1986 | Davis et al. |
| 4,624,661 A | 11/1986 | Arimond |
| 4,722,903 A | 2/1988 | Kudryk et al. |
| 4,761,158 A | 8/1988 | Schulte et al. |
| 4,861,335 A | 8/1989 | Reynolds |
| 5,020,362 A | 6/1991 | Hart et al. |
| 5,136,853 A | 8/1992 | Girardon et al. |
| 5,181,910 A | 1/1993 | Scanlon |
| 5,244,463 A | 9/1993 | Cordner, Jr. et al. |
| 5,324,258 A | 6/1994 | Rohrbough |
| 5,342,176 A | 8/1994 | Redlich |
| 5,387,909 A | 2/1995 | Neel et al. |
| 5,390,105 A | 2/1995 | Worley et al. |
| 5,502,365 A | 3/1996 | Nanbu et al. |
| 5,695,473 A | 12/1997 | Olsen |
| 5,826,713 A * | 10/1998 | Sunago .......... A61J 1/2089 206/222 |
| 5,906,589 A | 5/1999 | Gordon et al. |
| 6,031,707 A | 2/2000 | Meyer |
| 6,109,895 A | 8/2000 | Ray et al. |
| 6,176,845 B1 | 1/2001 | Kriesel et al. |
| 6,202,708 B1 | 3/2001 | Bynum |
| 6,260,004 B1 | 7/2001 | Hays et al. |
| 6,341,802 B1 | 1/2002 | Matkovich |
| 6,454,377 B1 | 9/2002 | Ishizaki |
| 6,555,986 B2 | 4/2003 | Moberg |
| 6,592,542 B2 | 7/2003 | Childers et al. |
| 6,595,756 B2 | 7/2003 | Gray et al. |
| 6,615,114 B1 | 9/2003 | Skiba et al. |
| 6,757,665 B1 | 6/2004 | Unsworth et al. |
| 6,835,049 B2 | 12/2004 | Ray |
| 7,056,890 B2 | 6/2006 | Najarian |
| 7,099,852 B2 | 8/2006 | Unsworth et al. |
| 7,151,963 B2 | 12/2006 | Havel et al. |
| 7,169,128 B2 | 1/2007 | Kriesel et al. |
| 7,220,244 B2 | 5/2007 | Kriesel |
| 7,220,245 B2 | 5/2007 | Kriesel |
| 7,290,993 B2 | 11/2007 | Vogeley et al. |
| 7,316,245 B2 | 1/2008 | Bivin |
| 7,470,253 B2 | 12/2008 | Kriesel et al. |
| 7,481,244 B2 | 1/2009 | Bivin |
| 7,513,273 B2 | 4/2009 | Bivin |
| 7,553,818 B2 | 6/2009 | Najarian |
| 7,581,434 B1 | 9/2009 | Discenzo et al. |
| 7,659,256 B2 | 2/2010 | Najarian |
| 7,674,776 B2 | 3/2010 | Najarian |
| 7,694,938 B2 | 4/2010 | Kriesel et al. |
| 7,735,522 B2 | 6/2010 | Bivin et al. |
| 7,776,006 B2 | 8/2010 | Childers et al. |
| 7,776,029 B2 | 8/2010 | Whitehurst et al. |
| 7,789,853 B2 | 9/2010 | Kriesel |
| 7,828,770 B2 | 11/2010 | Bivin et al. |
| 7,828,772 B2 | 11/2010 | Kriesel et al. |
| 7,833,195 B2 | 11/2010 | Kriesel et al. |
| 7,837,653 B2 | 11/2010 | Kriesel et al. |
| 7,896,843 B2 | 3/2011 | Kriesel et al. |
| 7,922,462 B2 | 4/2011 | Preuthun et al. |
| 7,944,366 B2 | 5/2011 | Krulevitch et al. |
| 7,993,304 B2 | 8/2011 | Kriesel et al. |
| 8,007,247 B2 | 8/2011 | Sarkinen et al. |
| 8,029,468 B2 | 10/2011 | Kriesel et al. |
| 8,057,435 B2 | 11/2011 | Kriesel et al. |
| 8,083,503 B2 | 12/2011 | Voltenburg, Jr. et al. |
| 8,083,717 B2 | 12/2011 | Kriesel |
| 8,100,890 B2 | 1/2012 | Kriesel et al. |
| 8,105,280 B2 | 1/2012 | Iddan et al. |
| 8,114,052 B2 | 2/2012 | Bivin et al. |
| 8,123,723 B2 | 2/2012 | Bivin et al. |
| 8,133,204 B1 | 3/2012 | Kriesel |
| 8,142,398 B1 | 3/2012 | Kriesel |
| 8,167,168 B2 | 5/2012 | Reynolds |
| 8,197,445 B2 | 6/2012 | Kriesel et al. |
| 8,211,059 B2 | 7/2012 | Kriesel et al. |
| 8,226,609 B2 | 7/2012 | Kriesel et al. |
| 8,231,575 B2 | 7/2012 | Kriesel |
| 8,246,573 B2 | 8/2012 | Ali et al. |
| 8,287,521 B2 | 10/2012 | Kriesel et al. |
| 8,292,848 B2 | 10/2012 | Kriesel et al. |
| 8,292,876 B2 | 10/2012 | Kriesel et al. |
| 8,303,535 B2 | 11/2012 | Both et al. |
| 8,317,753 B2 | 11/2012 | Kriesel et al. |
| 8,353,619 B2 | 1/2013 | Lauglarn, Jr. et al. |
| 8,356,733 B2 | 1/2013 | Py et al. |
| 8,361,009 B2 | 1/2013 | Lee et al. |
| 8,377,043 B2 | 2/2013 | Kriesel et al. |
| 8,388,571 B2 | 3/2013 | Joshi et al. |
| 8,388,578 B2 | 3/2013 | Joshi et al. |
| 8,403,887 B2 | 3/2013 | Kriesel et al. |
| 8,480,656 B2 | 7/2013 | Kriesel |
| 8,622,965 B2 | 1/2014 | Kriesel |
| 8,672,885 B2 | 3/2014 | Kriesel et al. |
| 8,821,454 B2 | 9/2014 | Kriesel et al. |
| 8,986,252 B2 | 3/2015 | Cummings et al. |
| 9,011,379 B2 | 4/2015 | Hariharesan et al. |
| 9,238,101 B2 | 1/2016 | Hariharesan et al. |
| 9,737,655 B2 | 8/2017 | Clemente et al. |
| 9,775,946 B2 | 10/2017 | McNall, III et al. |
| 9,814,832 B2 | 11/2017 | Agard et al. |
| 9,987,416 B2 * | 6/2018 | McNall, III .......... A61M 39/18 |
| 2003/0030272 A1 | 2/2003 | Johnson et al. |
| 2003/0161744 A1 | 8/2003 | Vilks et al. |
| 2004/0133166 A1 | 7/2004 | Moberg et al. |
| 2004/0260233 A1 | 12/2004 | Garibotto et al. |
| 2005/0096583 A1 | 5/2005 | Demers et al. |
| 2005/0151105 A1 | 7/2005 | Ryan et al. |
| 2005/0192561 A1 | 9/2005 | Mernoe et al. |
| 2005/0277882 A1 | 12/2005 | Kriesel |
| 2006/0030838 A1 | 2/2006 | Gonnelli |
| 2006/0052322 A1 | 3/2006 | Roth et al. |
| 2007/0112301 A1 | 5/2007 | Preuthun et al. |
| 2007/0235083 A1 | 10/2007 | Dlugos |
| 2008/0078781 A1 | 4/2008 | Py et al. |
| 2008/0083788 A1 | 4/2008 | Py et al. |
| 2008/0086087 A1 | 4/2008 | Spohn et al. |
| 2008/0116225 A1 | 5/2008 | Py et al. |
| 2008/0221522 A1 | 9/2008 | Moberg et al. |
| 2008/0287870 A1 | 11/2008 | Kallesoe et al. |
| 2008/0294098 A1 | 11/2008 | Sarkinen et al. |
| 2008/0306359 A1 | 12/2008 | Zdeblick et al. |
| 2009/0090186 A1 | 4/2009 | Linzenkirchner et al. |
| 2009/0093792 A1 | 4/2009 | Gross et al. |
| 2009/0112163 A1 | 4/2009 | Bivin et al. |
| 2009/0124994 A1 | 5/2009 | Roe |
| 2009/0131769 A1 | 5/2009 | Leach et al. |
| 2009/0247982 A1 | 10/2009 | Krulevitch et al. |
| 2010/0030299 A1 | 2/2010 | Covalin |
| 2010/0042068 A1 | 2/2010 | Friebe et al. |
| 2010/0130905 A1 | 5/2010 | Nuernberger et al. |
| 2010/0176754 A1 | 7/2010 | Navarra et al. |
| 2010/0300702 A1 | 12/2010 | Andrews et al. |
| 2011/0262535 A1 | 10/2011 | Najarian et al. |
| 2011/0264006 A1 | 10/2011 | Ali et al. |
| 2011/0282284 A1 | 11/2011 | Kriesel et al. |
| 2011/0282300 A1 | 11/2011 | Kriesel et al. |
| 2011/0319881 A1 | 12/2011 | Johnston |
| 2012/0109099 A1 | 5/2012 | Rogers et al. |
| 2012/0130341 A1 | 5/2012 | Whitley |
| 2012/0196881 A1 | 8/2012 | Najarian et al. |
| 2013/0218123 A1 | 8/2013 | Beiriger |
| 2013/0296792 A1 | 11/2013 | Cabiri et al. |
| 2013/0296803 A1 | 11/2013 | Kriesel |
| 2013/0331823 A1 | 12/2013 | Askem et al. |
| 2014/0058318 A1 | 2/2014 | Yodfat et al. |
| 2014/0213975 A1 | 7/2014 | Clemente et al. |
| 2014/0241923 A1 | 8/2014 | Nzike et al. |
| 2014/0296787 A1 | 10/2014 | Agard et al. |
| 2014/0301913 A1 | 10/2014 | Williams, Jr. et al. |
| 2014/0318995 A1 * | 10/2014 | Eilertsen .......... A61J 1/2096 206/219 |
| 2015/0174304 A1 | 6/2015 | Askem et al. |

(56) References Cited

U.S. PATENT DOCUMENTS

| | | |
|---|---|---|
| 2016/0095977 A1 | 4/2016 | Mcnall et al. |
| 2016/0144094 A1 | 5/2016 | Margolin et al. |
| 2016/0220753 A1 | 8/2016 | Ambrosina et al. |
| 2018/0028747 A1* | 2/2018 | Hanson ................. A61M 5/158 |
| 2020/0093558 A1* | 3/2020 | Naygauz ............... A61J 1/2089 |

* cited by examiner

VARIABLE RATE DISPENSER WITH ASEPTIC SPIKE CONNECTOR ASSEMBLY

FIELD OF THE INVENTION

The present invention relates generally to medical equipment, and more particularly to devices for dispensing drugs to a patient.

BACKGROUND OF THE INVENTION

Precise infusion of volumes of liquid drug or medication through an administration line is usually accomplished by an infusion pump. Traditional infusion pumps make use of a flexible infusion bag suspended above the patient. For many medicaments and drugs, a pharmacist, nurse, doctor, or other medical professional is required to attach and couple the bag to the pump, making connections between the two which may be contaminated. This can involve wrapping a tubing line around a peristaltic pump, mixing or diluting drugs, connecting fittings, and other activities which are susceptible to medication errors and contamination risks. Other problems exist with conventional pumps. For example, periodic monitoring of the apparatus by a nurse, doctor, or other medical professional is required to detect malfunctions of the infusion pump.

Accordingly, over the years, infusion pumps developed into increasingly more complex devices of great expense and sophistication. Such devices have many features, options, and programmability possibilities. While those capabilities can be advantageous in providing a range of customization to medication administration, they also can potentially lead to user error and the possibility of patient harm, injury, or death.

Complicated infusion pumps also typically require many time-consuming steps for setup. Increased preparation requirements increase the risk of contaminating the pump, the medication reservoir, the administration line, or other elements of the intravenous line system, posing an infection hazard to the patient. Although there has been an amount of innovation for small volume infusion and injection systems, there are not many options for systems handling larger volumes. An improved system for providing a convenient, reliable, accurate, and sterile infusion of liquid medication is needed.

SUMMARY OF THE INVENTION

A dispenser includes a container with an endwall and a cap covering the endwall. The cap has an aperture over the endwall and a first film covering the aperture. A hood over the cap has a barrel defining a bore which is coaxially aligned with the aperture, a second film sealing the bore, and a gasket compressed behind the second film. A spike is carried for movement in the barrel between retracted and advanced positions. The dispenser has first and second conditions. In the first condition, the first and second films are against each other and seal the aperture and barrel, and in the second condition, the first and second films are away, unsealing the aperture and the barrel. When the dispenser is in the second condition and the spike moves from the retracted position to the advanced position, the spike pierces the endwall.

The above provides the reader with a very brief summary of some embodiments discussed below. Simplifications and omissions are made, and the summary is not intended to limit or define in any way the scope of the invention or key aspects thereof. Rather, this brief summary merely introduces the reader to some aspects of the invention in preparation for the detailed description that follows.

BRIEF DESCRIPTION OF THE DRAWINGS

Referring to the drawings.

DETAILED DESCRIPTION

Figure 1:
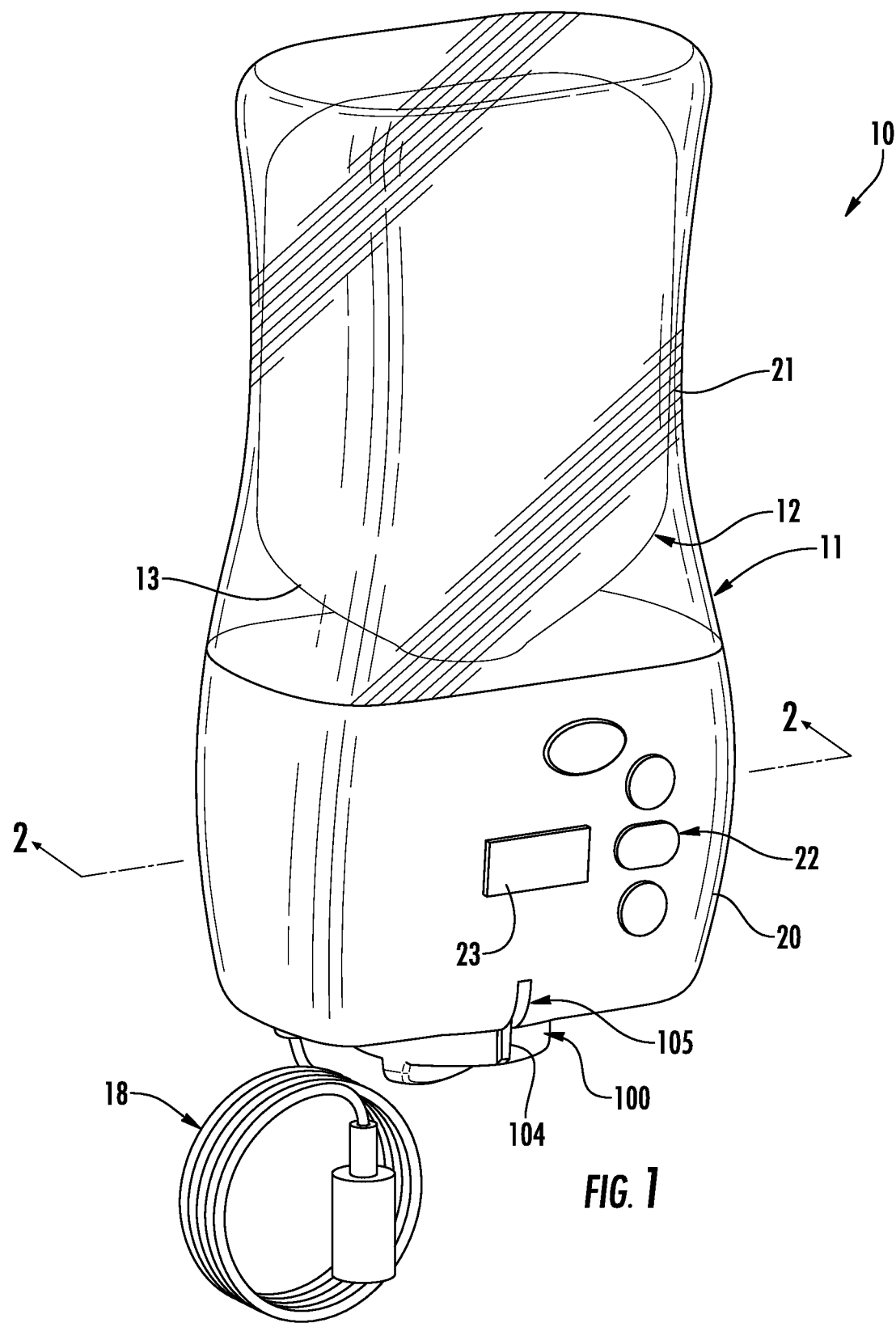
FIG. 1 is a front perspective view of a dispenser.
Figure 2:
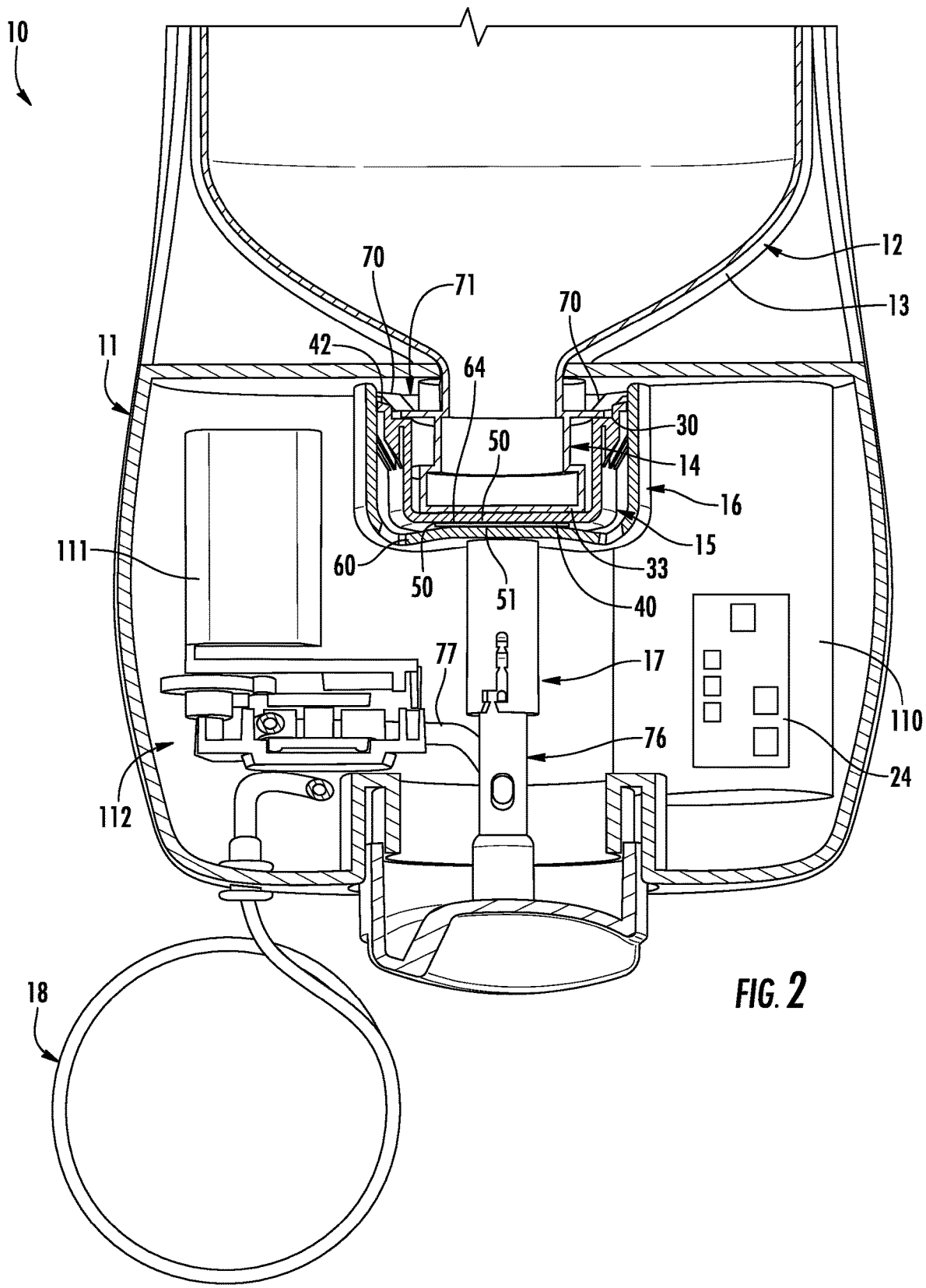
FIG. 2 is a section view of the dispenser taken along the line 2-2 in FIG. 1.

Reference now is made to the drawings, in which the same reference characters are used throughout the different figures to designate the same elements. FIG. 1 illustrates a front perspective view of a variable rate medication dispenser 10 (hereinafter, the "dispenser 10") useful for delivering a liquid medication to a patient via an administration line at a controlled flow rate. FIG. 2 illustrates a lower portion of the dispenser 10 in section view taken along the line 2-2 in FIG. 1. The dispenser 10 includes a housing 11, a container 12 including a reservoir 13, a head 14 fit over the container 12, a cap 15 fit over the head 14, and a hood 16 fit over both the cap 15 and head 14, where the hood 16 includes a barrel 17 extending away from the container 12. An administration line 18 exits the dispenser 10 and terminates in a fitting (not shown), such as a luer fitting, for coupling to a fitting on a patient. The dispenser 10 shown and described herein is preferably a prefilled, sterile, single-use, disposable infusion pump, and its various structural elements and features are uniquely constructed and arranged for these purposes.

The housing 11 includes a lower, preferably opaque body 20 and an upper, preferably transparent cover 21. The body 20 is preferably of one- or two-piece construction, and it houses and conceals most of the electronic, electrical, and mechanical components of the dispenser 10. The cover 21, in contrast, is disposed over the reservoir 13 of the container 12, so that a patient or health worker can easily see the amount of medication in the reservoir 13, yet the cover 21 is rigid to protect the container 12 from impact or other damage.

A flat face on the front of the housing 11 carries the user interface with input and output information and control. Four buttons 22, are shown in an exemplary arrangement, and they control operation of the dispenser 10. The buttons 22 allow a medical worker to activate the dispenser 10, select a mode, increment or decrement the flow rate, and start, pause, stop, or restart operation of the dispenser 10. Information, such as medication volume, warnings, and fault conditions, is displayed on a display screen 23, which is preferably an LCD display screen. In some embodiments, the user interface may also include auditory or haptic feedback. The buttons 22 and display screen 23 shown and described are non-limiting, and other control buttons and displays may be suitable as well. The buttons 22 and display screen 23 are electronically coupled to a printed circuit board 24 within the body 20 which is, in turn, electronically coupled to some of the components in the body 20 of the dispenser 10.

The components in the body 20 operate to draw medication from the container 12 and pump it to a patient. Turning now to FIG. 2 and also to FIGS. 3A and 3B, the container 12 includes a reservoir 13 and a head 14 integrally and monolithically formed to the reservoir 13. In a preferred embodiment, the container 12 is a blow-fill-seal container which can collapse as medication is drawn from it, but in other embodiments, the container 12 may be a syringe, vial, rigid enclosure, or some other structure. The reservoir 13 is the upper portion of the container 12, disposed mostly above the body 20 and within the cover 21, while the head 14 is disposed just below the top of the body 20. The reservoir 13 is typically between approximately two hundred fifty milliliters and four hundred milliliters in volume, but may be between approximately twenty milliliters and five hundred milliliters in other embodiments, or even more or less depending on the purpose of the particular dispenser 10. The container 12 is constructed from a material or combination of materials having rigidity, light weight, and high strength, such as plastic and high-density polyethylene ("HDPE") or polypropylene in particular. In some embodiments, films or layers are applied to the reservoir 13 to prevent the transmission of light, gas, or other destructive or harmful elements into the medication. An oxygen absorber can also be included in shipping packaging for the dispenser 10 to further reduce the exposure of the dispenser 10 to oxygen.

The head 14 is integrally and monolithically fit to the reservoir 13, thereby cooperatively defining the container 12. The head 14 includes a wide annular flange 30 at its base, proximate to the reservoir 13, and a neck 31 projecting from the flange 30 to an enlarged end 32 which has an outer diameter slightly larger than that of the neck 31 but less than that of the flange 30. The end 32 terminates in a pierceable endwall 33. The endwall 33 is flat, circular, smooth, and formed without discontinuities or irregularities. The endwall 33, like the rest of the monolithic container 12, is formed from HDPE, polypropylene, or a material having like characteristics.

The cap 15 is fit over the container 12 at the head 14 and covers this endwall 33. The cap 15 includes an endwall 40 and a continuous sidewall 41 extending from that endwall 40 to a flared terminal lip 42 opposite the endwall 40, defining an opening into an interior 43 of the cap 15, the interior 43 being bound by an inner surface 44 of the cap 15. Along an outer surface 45 of the cap 15 are a plurality of axially-extending ribs projecting from the lip 42 down the sidewall 41 and toward the endwall 40.

The endwall 40 has an aperture 46 at its geometric center. The aperture 46 passes entirely through the endwall 40 from the inner surface 44 to the outer surface 45. A longitudinal axis A is registered through the aperture 46, and indeed, through both the container 12 and the hood 16, too. The container 12, cap 15, and hood 16 generally have rotational symmetry with respect to the longitudinal axis A, except for some of the features explicitly described herein. The aperture 46 has an inner diameter sized to closely receive a spike 75 which moves through the hood 16 to pass through the aperture 46 and pierce the endwall 33 of the container 12, as is described in more detail later.

The cap 15 is hermetically welded onto the head 14 of the container 12. The container 12 carries the medication and is filled prior to formation or closure of the cap 15. Once the container is filled, the head 14 is inserted into the interior 43 of the cap 15. The outer surface of the endwall 33 of the container 12 is brought into close proximity with the inner surface 44 of the endwall 40 of the cap 15, such that the two endwalls 33 and 40 are nearly placed in direct, continuous, and flush contact with each other. This registers the lip 42 of the cap 15 against the flange 30 on the container 12; the sidewall 41 of the cap 15 fits over the end 32 and neck 31 of the container but the lip 42 terminates just in front of the flange 30, such that they are in continuous contact. Along this annular contact, a weld is formed, such as by plastic welding, sonic welding, or other welding process producing a hermetic seal. Sealing the cap 15 against the head 14 produces a continuous contact fit between the endwalls 33 and 40 to inhibit accidental fluid migration from between the cap 15 and head 14.

A first film 50 at least partially covers the endwall 40. The film 50 is a peelable thin plastic film which can be peeled and removed from the dispenser 10 when so desired. The film 50 overlies the aperture 46 and a portion of the endwall 40 surrounding the aperture 46. The film 50 has an upper surface and a lower surface. In the view shown in FIG. 3A, the upper surface is the one which is directed toward and overlies the aperture 46, and the lower surface is directed away therefrom. The film 50 covers the aperture 46 such that it acts as a barrier preventing the passage of fluids into and out of the aperture 46 when in place over the aperture 46. Generally, after the container 12 is filled with medicine, the cap 15 is applied to the head 14, the film 50 is applied to the endwall 40, and the container 12 is sterilized, preferably with autoclaving. Because the film 50 seals the aperture 46, the aperture 46 is sterilized as well, and it maintains such sterility until at least such time as the film 50 is removed, but actually longer because of separate sterilization and assembly techniques in the dispenser 10, as are explained below.

In some embodiments, the film 50 may lie flat against the endwall 40 as a single layer of film. In other preferred embodiments, however, the film 50 is actually folded upon itself, so that a folded end of the film 50 is folded over an end portion of the film 50, and the folded end of the film 50 is adhered to the endwall 40 of the cap 15 around the aperture 46. In such embodiments, the lower surface of the film 50 is against the endwall 40 immediately surrounding the aperture 46 because this is the folded end of the film 50, but a portion of the upper surface of the remainder of the film 50 is against the remainder as the film 50 is disposed outward along the endwall 40 from the aperture 46. Indeed, the film 50 extends away from the aperture 46 and and the cap 15, where it is available to be pulled. When the film 50 is pulled, the folded end peels off from around the aperture 46, thereby opening the aperture 46. However, peeling the film 50 away from the endwall 40 does not alone couple the aperture 46 in fluid communication with another part of the dispenser 10. More action is required because, at least, there is a second film 51.

This second film 51 isolates the hood 16—and everything behind or below the hood 16—from the cap 15 and container 12. The film 51 is structurally identical to the film 50, but it covers a bore in the hood 16. While in some embodiments a single layer of film 50 may overlie the bore and parts of the hood 16, a folded version of the film 51 is more preferably used. The film 51 must also be removed to couple the aperture 46 in fluid communication with other parts of the dispenser 10. This is explained in detail after a discussion of the hood 16.

Figure 3A:
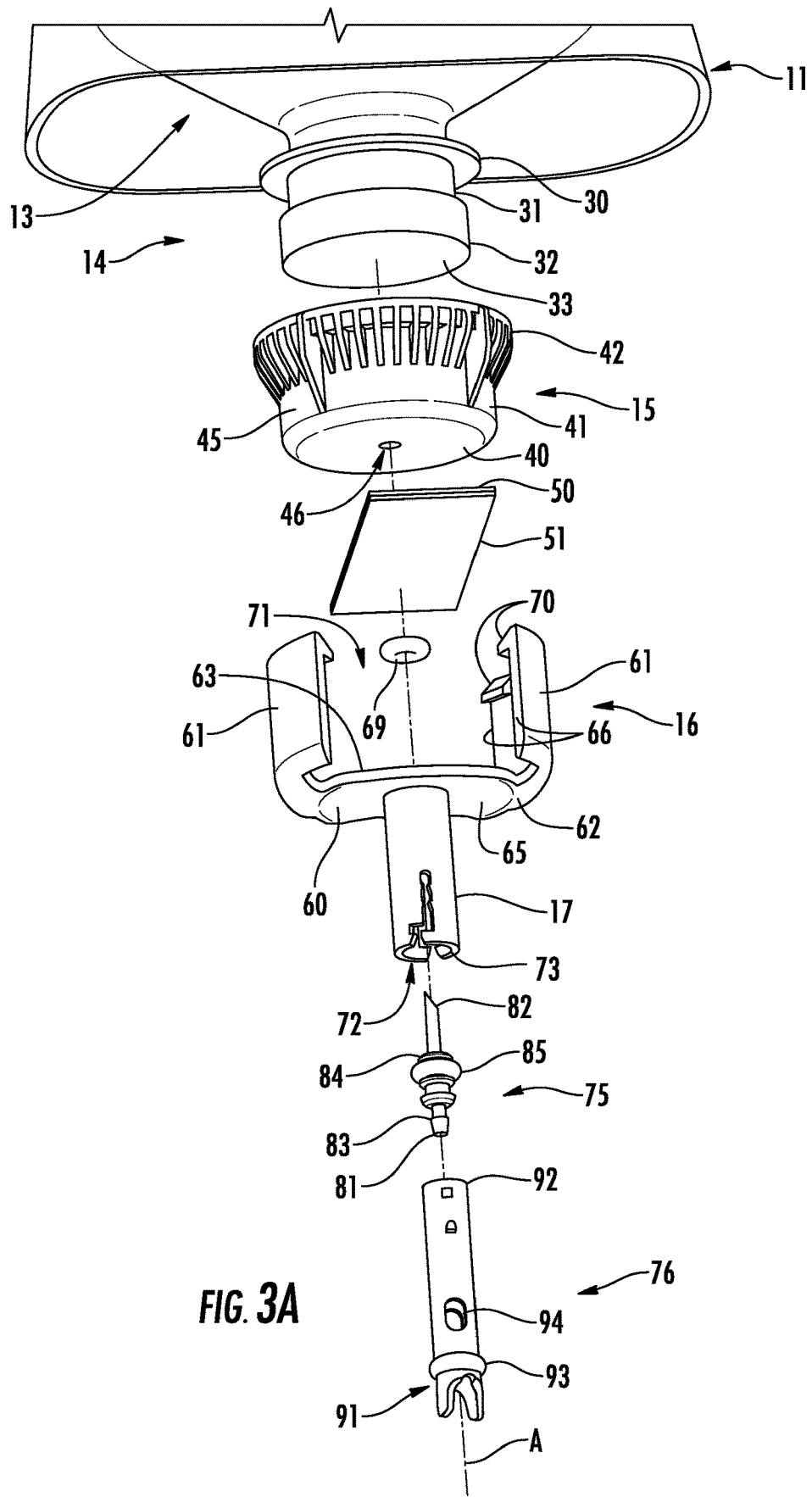
FIGS. 3A and 3B are exploded top and bottom perspective views of a lower portion of the dispenser.
Figure 3B:
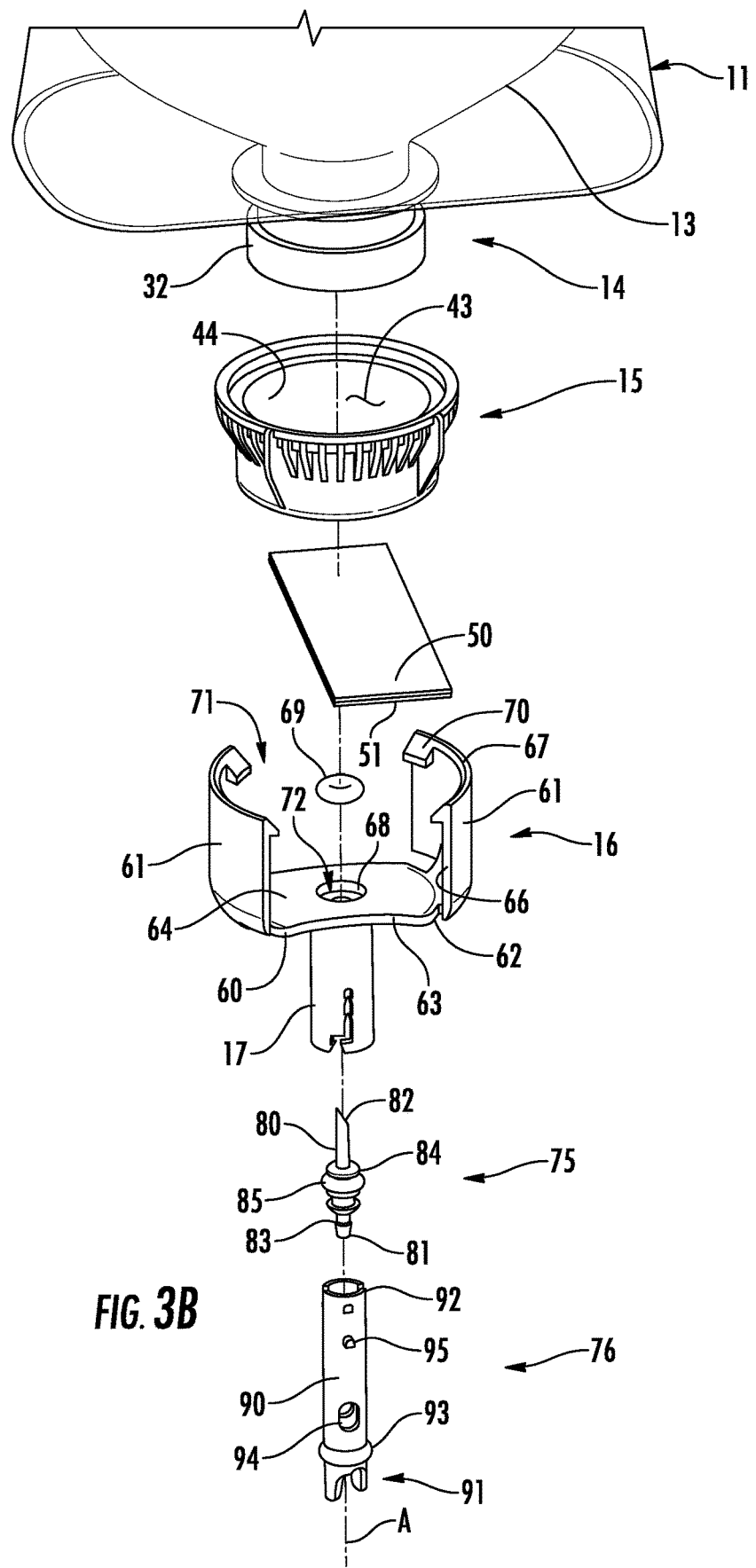

Referring primarily to FIGS. 3A and 3B, the hood 16 has a flat base 60, projecting opposed clasps 61, and the depending barrel 17 opposite the clasps 61. The base 60 is oval, has opposed outwardly-curved or convex ends 62 and opposed inwardly-curved or concave sides 63 extending between the ends 62. The base 60 further includes an inner surface 64 and an opposed outer surface 65; the inner surface 64 is flat, smooth, and flanked by the opposed clasps 61 while the outer surface 65 is similarly flat, smooth, but directed away from the clasps 61.

The clasps 61 extend from the base 60 at the opposed ends 62. The clasps 61 are identical but opposite, and only one will be described with the understanding that the description applies equally to both. The clasp 61 is formed integrally and monolithically to the base 60 as a perpendicular extension thereof. The clasp 61 is convex, corresponding to the curvature of the convex end 62, and has a sidewall with opposed sides 66 that extend away from the inner surface 64 to a convex top edge 67. Formed on the top edge 67, and overhanging the sidewall, are two tabs 70. The base 60 and clasps 61 cooperate to surround and define a hold 71 of the hood 16. The tabs 70 project into the hold 71 to define its upper extremity, while the base 60 opposes, bordering the lower extremity of the hold 71. The clasps 61 are strong yet resilient, and are constructed from a material that allows the clasps 61 to flex in a direction transverse to their length between the base 60 and the top edge 67, such that the clasps 61 can be snapped over the head 14 and cap 15.

The barrel 17 depends downwardly from the base 60, opposite the clasps 61. The barrel 17 is an elongate cylinder, formed around a central bore 72 terminating in the base 60, through which it passes entirely. The bore 72 is registered along the longitudinal axis A and is thus both registered and coaxially aligned with the aperture 46. Opposite the barrel 17, formed into the inner surface 64 of the base 60, is an annular seat 68 encircling the bore 72. An o-ring or elastomeric gasket 69 is snugly received and slightly compressed in the seat 68. The barrel 17 depends to a flat bottom end 73, where it has a bayonet channel 74 to lock a spike 75 and bolt 76 which are carried within the bore 72. The bayonet channel 74 is described in more detail later, but includes a lateral channel portion and an axial channel portion to guide movement of the spike 75 and bolt 76 within the bore 72.

The spike 75 and bolt 76 are carried within the barrel 17 of the hood 16 for axial and rotational movement between a retracted position (shown in FIGS. 4A and 5A) and an advanced position (shown in FIGS. 4C and 5C) and operate to connect the reservoir 13 in fluid communication with the administration line 18. When the dispenser 10 is needed for use, the spike 75 and bolt 76 are driven through the barrel 17 into the advanced position to pierce the endwall 33 and couple tubing 77 in fluid communication with the container 12. Before that, however, the spike 75 and bolt 76 are retained in the retracted position behind the second film 51, behind which the sterility of the hood 16, spike 75, bolt 76, and tubing 77 is ensured and maintained.

The spike 75 has an elongate, cylindrical, hollow shaft 80 with a barbed bottom 81 and an opposed lumen 82 at the top. An annular barb 83 radially enlarges the outer diameter of the shaft 80 proximate the bottom 81, such that the tubing 77 fit over the barb 83 can be securely fit thereon with a tight, fluid-impermeable seal. Several annular flanges 84 project radially along the length of the shaft 80; between two of these flanges 84 is an o-ring or elastomeric gasket 85 having a compressible outer diameter. The shaft 80 terminates at its top in the lumen 82, which is beveled and sharp to pierce the endwall 33 of the container 12.

The spike 75 is mounted in the bolt 76. The bolt 76 is an elongate cylinder, having a hollow shaft 90 with an open bottom 91 and an opposed open top 92. Proximate the bottom 91, the shaft 90 has a bulb 93, which is a bulbous annular projection. Above the bulb 93 is a hole 94; the tubing 77 fit over the barb 83 of the spike 75 passes through this hole 94 when the dispenser 10 is fully assembled. Just above the hole 94 is a tab 95 projecting radially outward from the shaft 90. This tab 95 fits into and follows the bayonet channel 74 in the barrel 17 when the bolt 76 moves therein.

Figure 4A:
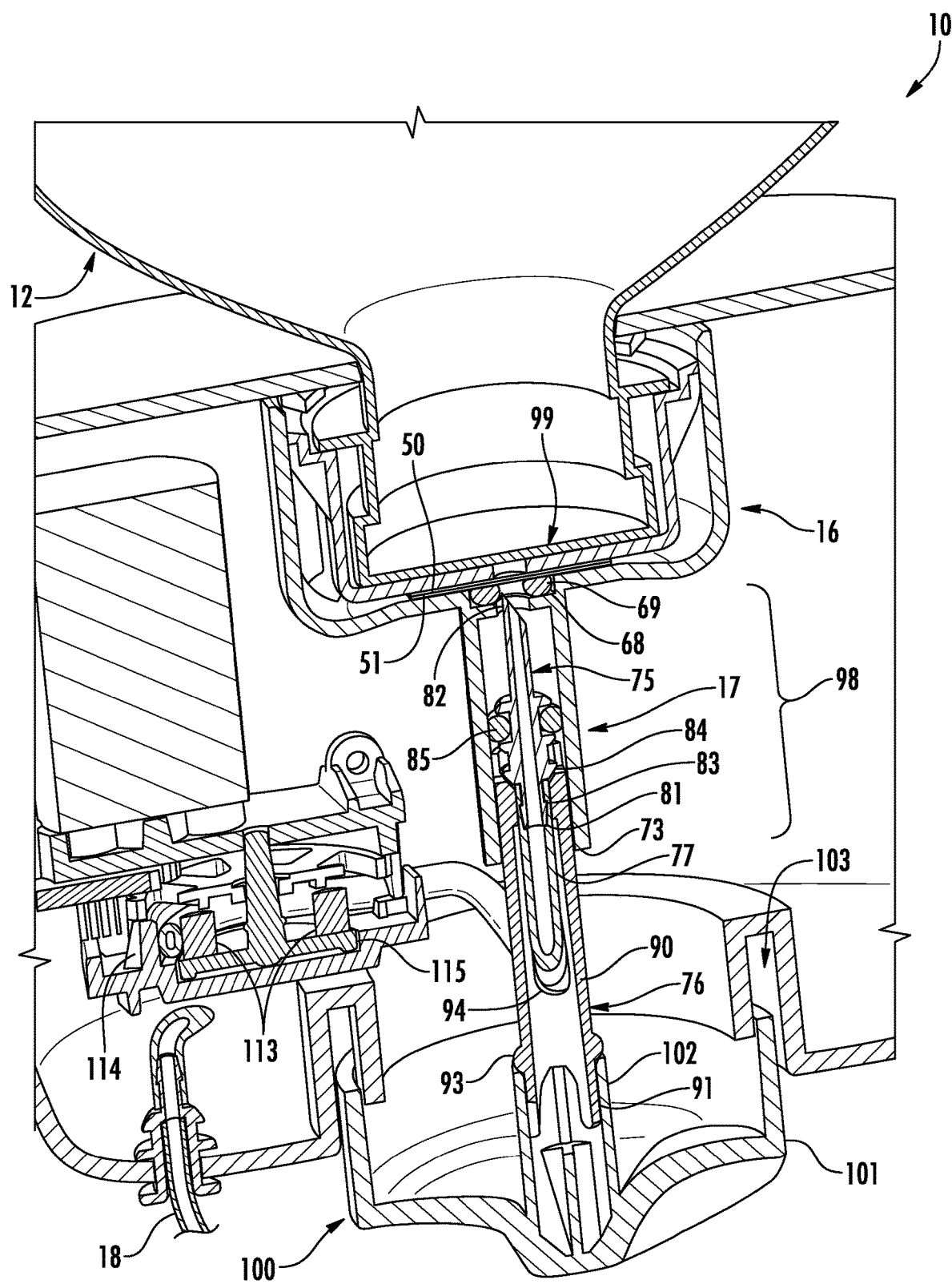
FIGS. 4A-4C are section views bisecting the dispenser showing a spike moving through various positions to aseptically pierce a container of the dispenser to allow medication to be drawn therefrom.

The spike 75 is snug-fit into the bolt 76. As best seen in FIG. 4A (a section view bisecting the dispenser 10 along the line 2-2 in FIG.), a free end of the tubing 77 is tight-fit onto the bottom 81 of the spike 75, over the barb 83, and against the bottom-most flange 84. The tubing 77 and spike 75 are both within the bolt 76, and so the free end of the tubing 77 is compressed between the spike 75 and the bolt 76, above the bottom end 73 of the barrel 17, forming a seal. The tubing 77 extends downward from the spike 75 and passes through the hole 94 in the shaft 90 of the bolt 76. The tubing 77 then is routed elsewhere through the dispenser 10 before it connects to the administration line 18. This routing allows the tubing 77 to move with the spike 75 and bolt 76 when those components move through the barrel 17.

The spike 75 and bolt 76 move in the barrel 17 only when a health worker causes them to move. The bottom 91 of the bolt 76 is set into a knob 100, shown best in FIG. 4A. The knob 100 has a large, graspable body 101 and an inner post 102 within the housing 11 extending upward into which the bolt 76 is set. The knob 100 is mounted for rotation within an annular seat 103 at the bottom of housing 11. The bottom 91 of the bolt 76 is press-fit within the post 102, and the post 102 abuts the bulb 93. Thus, when the knob 100 is rotated, the spike 75 and bolt 76 are similarly rotated; when the knob 100 is advanced upward into the housing 11, the spike 75 and bolt 76 are similarly advanced upward. As seen in FIG. 1, inadvertent advancement of the knob 100 is prevented by a tab 104 on the outside of the knob 100; the tab 104 must be aligned with and fit into a slot 105 on the outside of the housing 11 before the knob 100 can be advanced into the housing 11.

The above describes the container 12, the cap 15, the hood 16, the spike 75, bolt 76, and tubing 77, which make up a fluid communication path 98 within the dispenser 10. The dispenser 10 includes other components which act on the fluid communication path 98 to activate and control dispensation of medication to a patient. Referring to FIG. 2, the dispenser includes an energy storage means in the form of batteries or a battery 110, an electric motor 111, and a pump assembly 112. The tubing 77 is routed through the pump assembly 112, which is preferably a peristaltic pump with rollers 113 (shown in FIG. 4A) which compress the tubing 77 against a wall 114. The tubing 77 is constructed of a material or combination of materials having characteristics of flexibility, fluid impermeability, and compressibility, such as polyvinylchloride, polyurethane, silicone, or the like. The motor 111 operates to rotate a plate 115 in the pump assembly 112 to which the rollers 113 are mounted. In response, the rollers 113 rotate around, sequentially compressing and occluding the tubing 77 against the wall 114. The battery 110, motor 111, and pump assembly 112 are all electronically coupled to the printed circuit board 24, and so when the health worker interacts with the buttons 22 and display screen 23, the printed circuit board 24 controls the motor 111 in response.

Before the dispenser 10 is used, however, it must be assembled. Assembly preferably occurs in several stages. In one stage, the container 12 is filled with medication, the cap 15 is fit over the head 14 as described above, and the first film 50 is applied over the aperture 46 in the endwall 40 of the cap 15. The container 12 can contain and dispense medications such as 5FU (5-fluorouracil or fluorouracil), abatacept, acetominophen, acyclovir, alteplase, amikacin, amphotericin b, ampicillin, aprepitant, argatroban, aztreonam, aztreonam injection, belatacept, belimumab, bendamustine, bevacizumab, bivalirudin, bleomycin, bupivacaine, cabazitaxel, camptosar, carboplatin, carmustine, caspofungin, cefazolin, cefepime, cefmetazole, cefotetan, cefoxitin, cetuximab, chloramphenicol, cidofovir, ciprofloxacin, cisplatin, cladribine, clindamycin, cyclophosphamide, cytoxan, dacarbazine, daptomycin, daunorubicin, deferoxamine, dexmedetomidine, dexrazoxane, dobutamine, docetaxel, dopamine, doxorubicin, doxycycline, elelyso, elotuzumab, epirubicin, erbitux, ertapenem, erythromycin, etomidate, etoposide, etoposide phosphate, fentanyl, filgrastim, flagyl, fluconazole, fludarabine, fosaprepitant, foscarnet, furosemide, ganciclovir, gemcitabine, gemtuzumab ozogamicin, gentamicin, granisetron, hemin, ibritumomab tiuxetan, idarubicin, ifosfamide, imiglucerase, immune globulin, inamrinone, infliximab, intravenous immunoglobulin, ipilimumab, irinotecan, ketamine, leukine, levaquin, levobupivacaine, lidocaine, linezolid, meropenem, midazolam, mirinone, mitomycin, mitoxantrone, mylotarg, nafcillin, natalizumab, neupogen, nivolumab, norepinephrine, ofatumumab, ondansetron, oxacillin, oxalaplatin, paclitaxel, panitumumab, pertuzamab, plicamycin, polymyxin b, primaxin, propofol, quinupristin and dalfopristin, remifentanyl, rifampin, rituximab, ropivacaine, sodium valproate, streptozocin, synercid, taliglucerase alfa, teniposide, thiotepa, ticarcillin and clavulanate, tigecycline, tobramycin, topotecan, total parenteral nutrition, trastuzumab, trimetrexate, unasyn, vancomycin, vectibix, velaglucerase alfa, velcade, vinblastine, vinorelbine, vortezomib, vpriv, vumon, zoledronic acid, zosyn, or the like. It is noted that the above list of medications is not exclusive, and the dispenser 10 is suitable for use with other medications, other liquids such as saline solutions, and combinations of these or other medications or liquids. This container assembly can then be sterilized, preferably with autoclaving sterilization techniques. Once so sterilized, the medication, the aperture 46, and the portion of the endwall 33 behind and around the aperture 46 are maintained in sterility.

In another, separate stage, the fluid communication path 98 is assembled and sterilized. The gasket 69 is radially compressed slightly and applied to the seat 68 in the inner surface 64 of the hood 16 until it projects just beyond flush with the inner surface 64. The second thin film 51 is then applied over the gasket 69 and adhered to the inner surface 64 around the gasket 69 and the bore 72. The spike 75 is fit into the bolt 76. First, a free end of the tubing 77 is threaded through the hollow shaft 90 of the bolt 76 from the open bottom 91 through and out the open top 92. The tubing 77 is then fit over the barb 83 to secure a tight-fit engagement to the spike 75. The spike 75 is next moved, with its bottom 81 directed toward the top 92 of the bolt 76, into the bolt 76, until the tubing 77 is tightly compressed to ensure that the seal formed between the spike 75 and bolt 76 with the tubing 77 therebetween is fluid impermeable.

The spike 75 and bolt 76 are then introduced to the barrel 17 of the hood 16. The spike 75 is inserted into the bore 72 with the lumen 82 through the bottom end 73 first. The spike 75 and bolt 76 are advanced into the barrel 17 until the lumen 82 is disposed within the seat 68 and the gasket 69. In this disposition, the spike 75 is entirely contained within the length of the barrel 17, and a portion of the shaft 90 of the bolt 76 near the top 92 is within as well. The remainder of the shaft 90 projects out of the barrel 17, presenting the bottom 91 of the bolt 76 for the knob 100. The hood 16, spike 75, and bolt 76 are applied to the housing 10 so that the knob 100 can be installed. The post 102 of the knob 100 is pushed over the bottom 91 of the bolt 76 until it reaches the bulb 93, ensuring that the knob 100 is registered in the seat 103.

The tubing 77, which extends out of the bolt 76 through the hole 94, is routed through the pump assembly 112, ensuring that its length is placed between the rollers 113 and the wall 114. Preferably, the battery 110, motor 111, and printed circuit board 24 are not yet installed in the housing 11 at this point because this assemblage of components for the fluid communication path 98 is then subjected to gamma-ray sterilization. Once these parts are so sterilized, final assembly of the dispenser 10 can occur.

The battery 110, motor 111, and printed circuit board 24 are installed within the housing 11. Then, the container 12, cap 15, and first film 50 are applied to the housing 11. Referring to FIG. 2, the container 12 and cap 15 are moved downward into the hold 71 of the hood 16 in coaxial alignment with the hood 16, the spike 75, and the bolt 76. The cap 15 is moved downward into the hold 71 until the endwall 40 is proximate to the inner surface 64 of the base 60 of the hood 16, such that the first and second films 50 and 51 are in direct contact against each other. While the external surfaces of the first and second films 50 and 51 may not be sterile, they are only in contact with each other and thus do not affect the sterility of the medication above or the fluid communication path 98 below. When the films 50 and 51 are in contact with each other, the tabs 70 on the hood 16 snap over lip 42 of the cap 15 and the flange 30 of the container 12, thereby securely snap-fitting the hood 16 to the container 12.

Figure 5A:
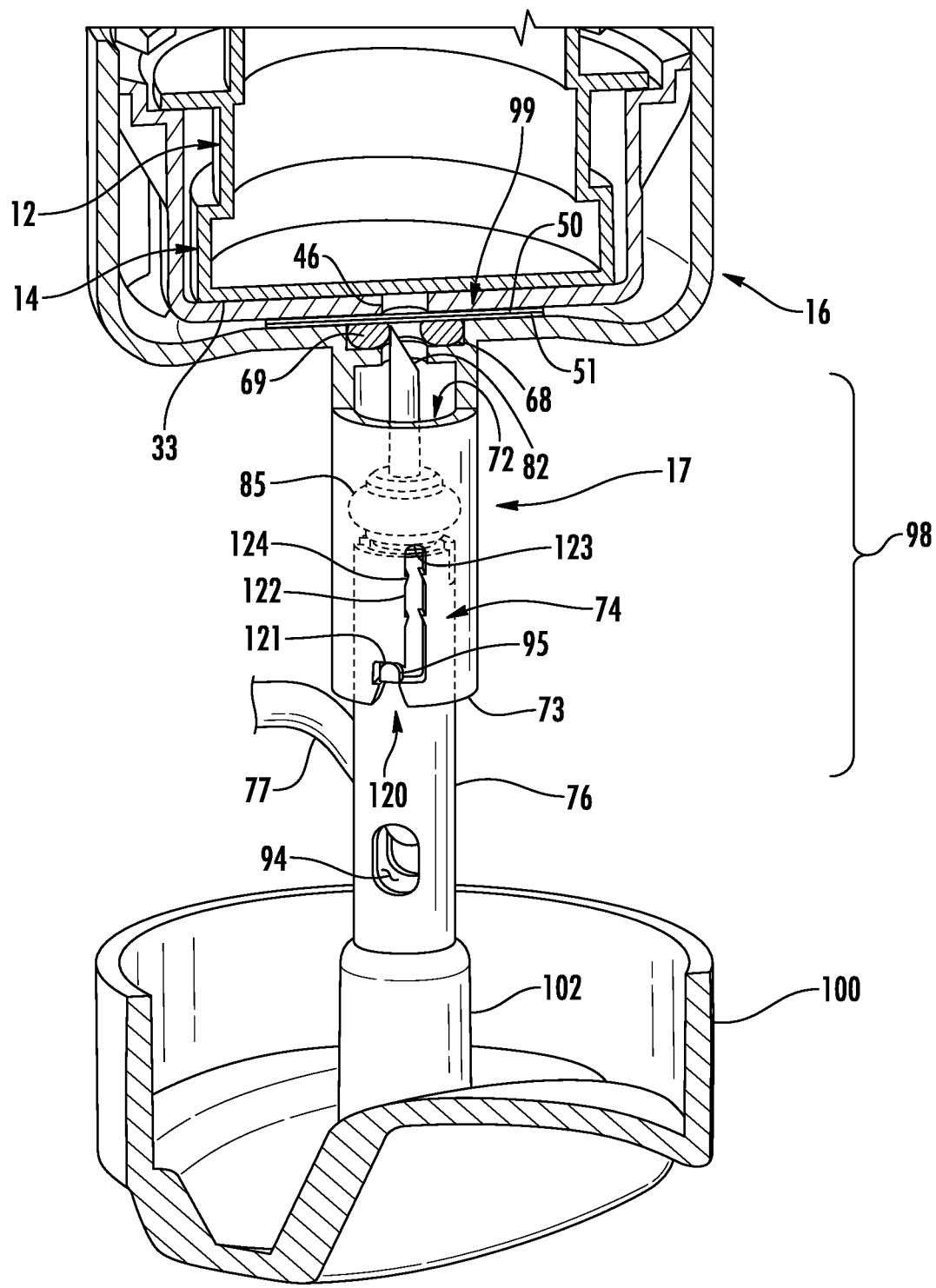
FIGS. 5A-5C are partial section views isolating portions of the dispenser as the spike moves through various positions to aseptically pierce a container of the dispenser to allow medication to be drawn therefrom.

This snap-fit engagement produces a compressive force between the endwall 40 and base 60. As such, the gasket 69 is compressed axially, and it produces a responsive force or bias axially outward, compressing the first and second films 50 and 51 against the cap 15. Moreover, these compressive and responsive forces compress the first and second films 50 and 51 into each other. At this point, the spike 75, the first and second films 50 and 51, and the gasket 69 define an aseptic spiking assembly 99 (as seen in FIGS. 4A and 5A), arranged in a first condition thereof with the first and second films 50 and 51 against each other and sealing the aperture 46 and bore 72, respectively, and with the spike 75 is in its retracted position. The aseptic spiking assembly 99 allows the two parts of the dispenser 10 to be coupled to each other, maintained in sterility, and later be coupled in fluid communication with each other in an aseptic fashion. Indeed, this defines a first condition of the dispenser 10 in which the first and second films 50 and 51 are against each other and seal the aperture 46 and the barrel 72. The dispenser 10 could be stored in this state for a prolonged period or could even be shipped and transported in this state for final preparation by a health worker when the dispenser 10 is needed in the hospital, clinic, etc. However, preferably, the first and second films 50 and 51 are removed soon after they have been brought together, thereby arranging the dispenser 10 into a second condition.

Sterility of the medication and the fluid communication path 98 is ensured even during removal of the first and second films 50 and 51; the non-sterile external surfaces of the first and second films 50 and 51 are peeled away in confrontation with each other such that they do not touch the endwall 40, the aperture 46, the seat 68, the gasket 69, or the bore 72. As such, the aperture 46 and bore 72 are unsealed and brought into open communication with each other, and brought together in sterility because their inner surfaces remain sterile, having not been exposed: the compressed gasket 69 immediately forms a seal with the endwall 40 surrounding the aperture 46 as the films 50 and 51 are peeled away. While the aperture 46 and bore 72 are brought into open communication with each other, however, they are not yet brought into fluid communication with each other. Indeed, mere removal of the films 50 and 51 does not accomplish this. Rather, the spike 75 must be advanced. As such, the dispenser 10 is now only in the second, storage, unready condition, as defined by the arrangement described above, and in which it can still be stored for long periods of time, is suitable to be transported, and can sit waiting for use. But it is not ready to be used. To move the dispenser 10 into a ready condition, the spike 75 must be advanced to pierce the endwall 33 after the films 50 and 51 have been removed.

Figure 5B:
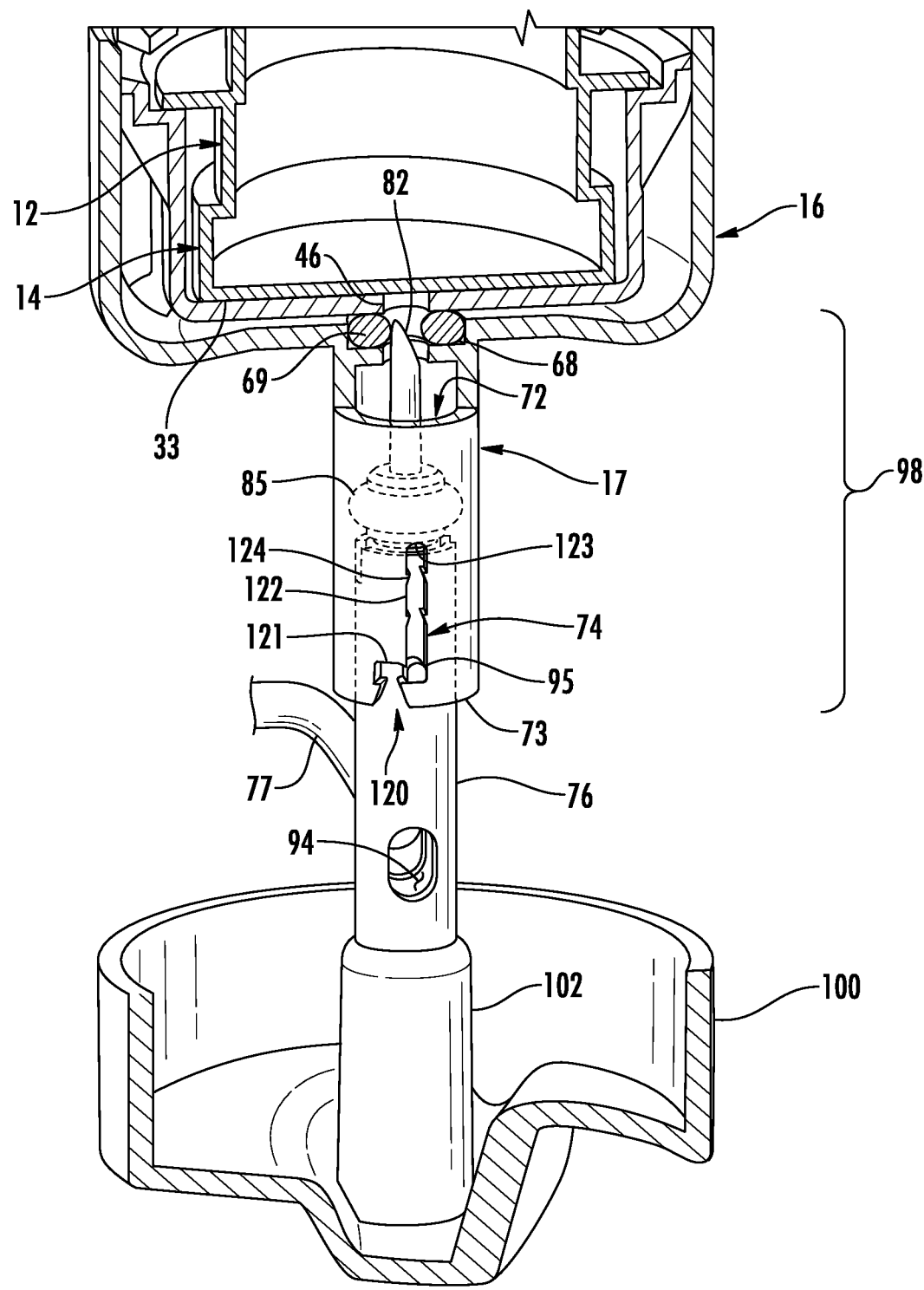
Figure 5C:
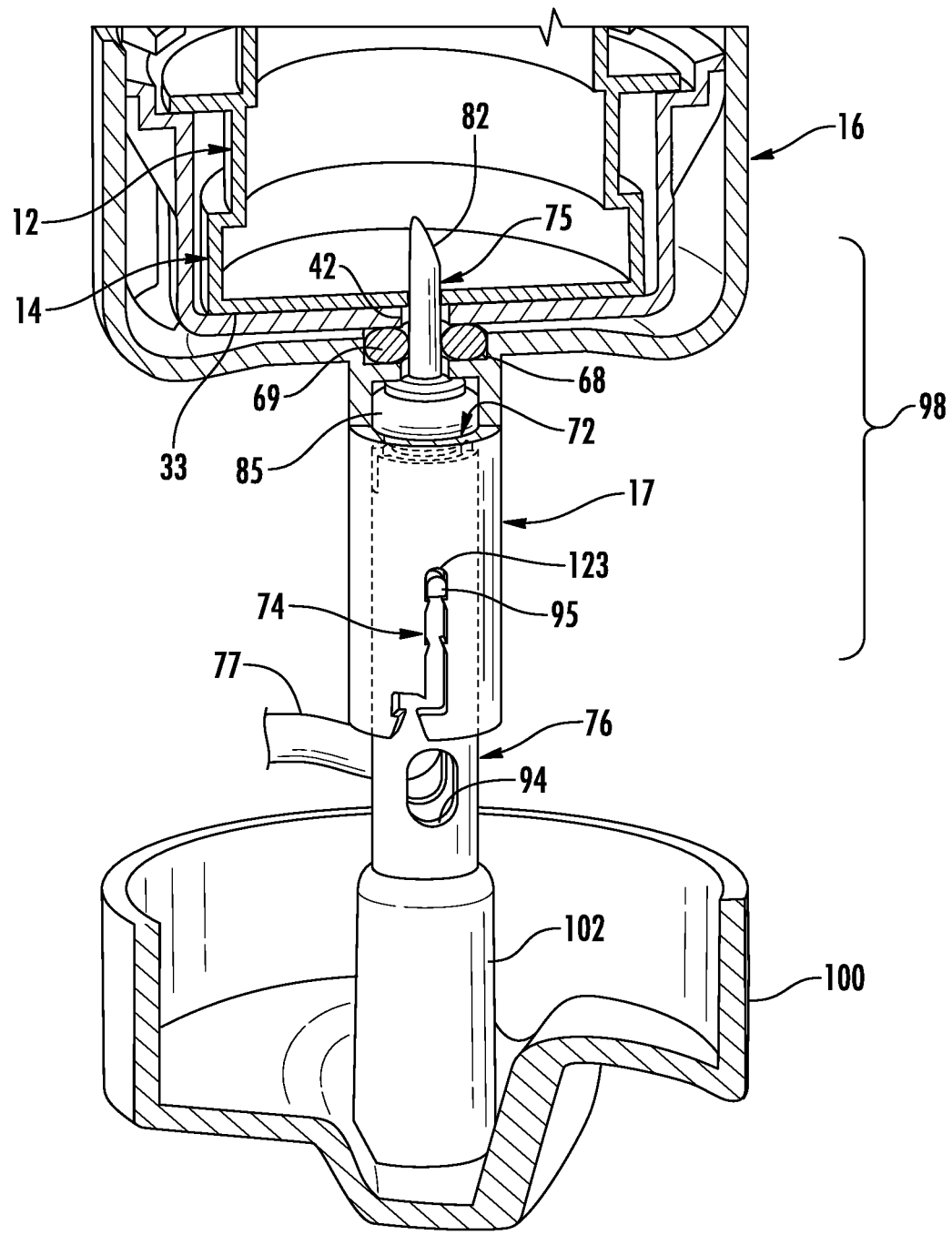

When the health worker has a dispenser 10 and is ready to use the dispenser 10, the health worker must first arrange the dispenser 10 from the unready condition to the ready condition. She does this by moving the spike 75 forward. The spike 75 moves through the barrel 17 and is guided in such movement by interaction of the bolt 76 in the bayonet channel 74. Referring to FIGS. 5A-5C, the structure of the bayonet channel 74 is shown, as well as the movement of the spike 75 and bolt 76 through it. The bayonet channel 74 includes an entrance 120, a lateral portion 121, and an axial portion 122. The entirety of the bayonet channel 74 is an opening in the side of the barrel 17, through which the tab 95 projects and travels. The entrance 120 is in communication with the end 73 of the barrel 17. The lateral portion 121 is formed perpendicular to the entrance 120 and parallel to the end 73, and it extends a short circumferential distance around the barrel 17 from the entrance 120 to the axial portion 122. The axial portion 122 then extends axially upward from the lateral portion 121 to an end 123. Along the length of the bayonet channel 74, its width or open dimension is constant, but for several sets of ratchet teeth 124. Each ratchet tooth 124 projects into the bayonet channel 74, thereby reducing its width. Moreover, each ratchet tooth 124 projects upwardly, thereby allowing the tab 95 to move in a direction from the entrance 120 to the end 123 but not back again. This prevents the spike 75 from being pulled out of the endwall 33 once it has pierced it. When the spike 75 and bolt 76 are initially inserted into the barrel 17 during assembly, the tab 95 is passed through the entrance 120.

Figure 4B:
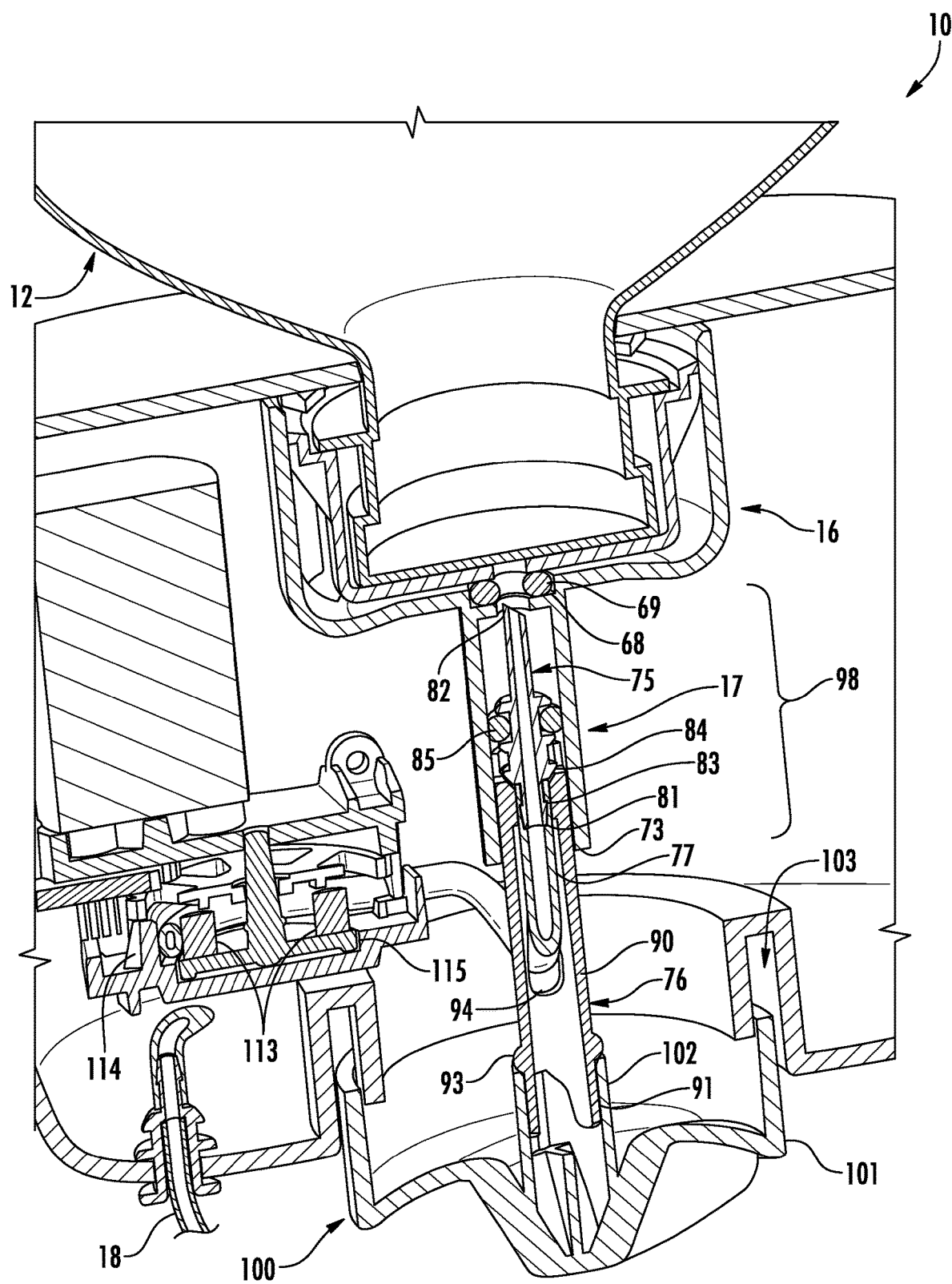
Figure 4C:
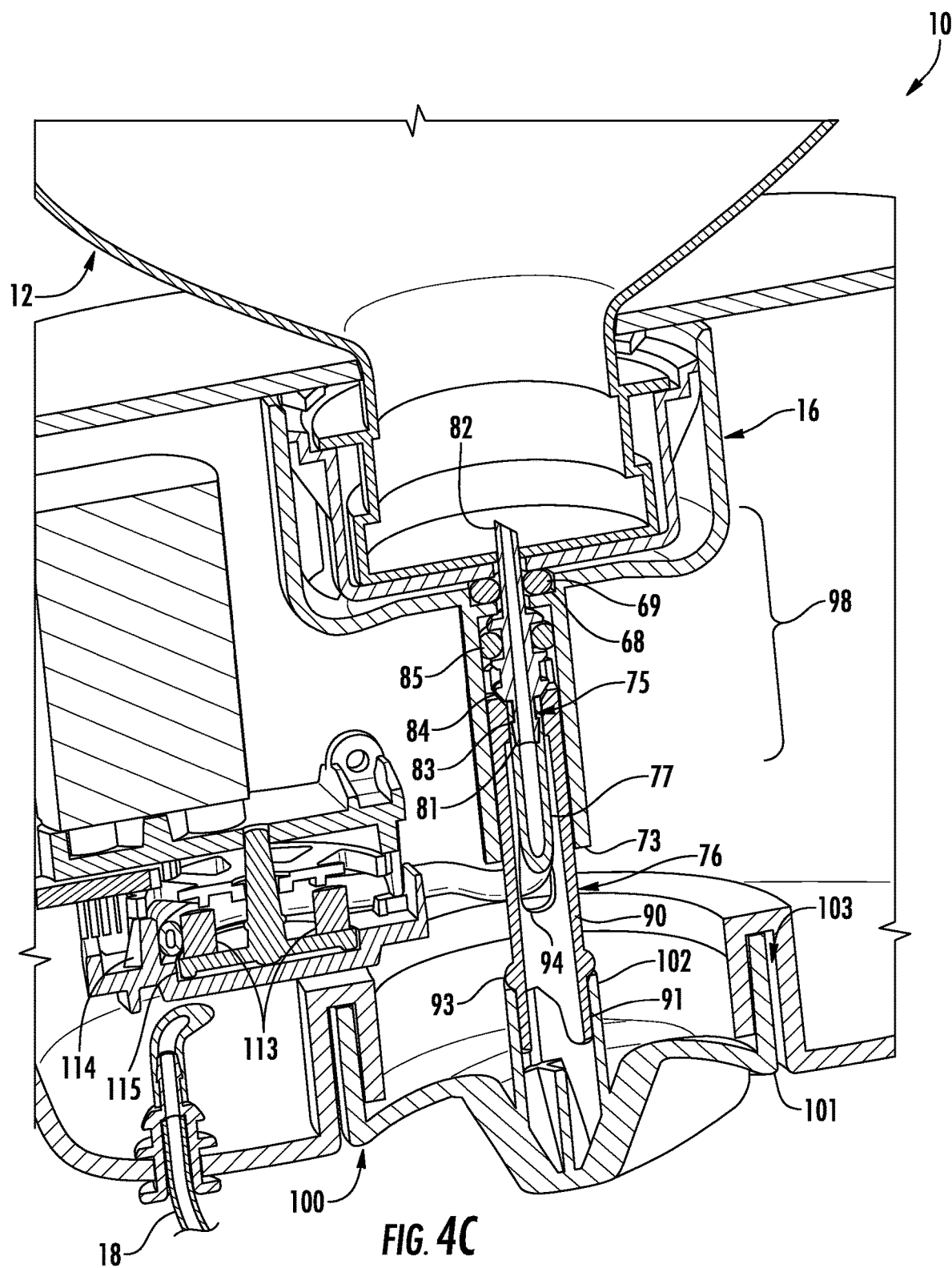

To arrange the dispenser 10 into the ready condition, the health worker rotates the knob 100 until the tab 104 on the knob 100 is aligned with the slot 105. This causes the tab 95 on the bolt 76 to rotate through the lateral portion 121 to below the axial portion 122 (see FIGS. 4B and 5B). This movement also closes an electrical connection between the battery 110 and the printed circuit board 24, thereby energizing the dispenser 10. The health worker then depresses the knob 100 into the housing 11, which moves the tab 95 through the axial portion 122 of the bayonet channel 74, past each of the ratchet teeth 124. Moreover, this advances the spike 75 axially, moving the lumen 82 through gasket 69 in the seat 68 of the hood 16, through the aperture 46, and through the endwall 33, and into the container 12, piercing the endwall 33 in the process (see FIGS. 5B and 5C). This arranges the aseptic spiking assembly 99 into a second condition in which the films 50 and 51 are away, unsealing the aperture 46 and bore 72, and the spike 75 is in the advanced position piercing the endwall 33 of the container 12. In the advanced position, the spike 75 is not only advanced but is rotated with respect to its position in the retracted position. In some embodiments, a spring may urge the spike 75 and bolt 76 forward. This movement places the container 12 in fluid communication with the tubing 77. Moreover, it does so aseptically, because the inner diameter of the gasket 69 is smaller than the outer diameter of the shaft 80 of the spike 75, ensuring that the gasket 69 closely receives the spike 75 in sealing contact as the spike 75 moves through it, and because the gasket 85 on the spike 75 within the bore 72 of the barrel 17 is compressed therein, also forming a seal as the spike 75 moves through the bore 75. These two gasket seals ensure the sterility established in the unready condition is maintained. Indeed, the gasket 69 alone makes sealing contact with the spike 75, the hood 16, and the cap 15.

With the lumen 82 inside the container 12, the dispenser 10 is arranged into the ready condition. The fluid communication path 98 is coupled in fluid communication with the medication in the container 12 and the dispenser 10 is energized by the battery 110. The dispenser 10 is now nearly ready to be used. Though the dispenser 10 has been shown and described throughout the drawings in a particular orientation (including with reference to terms such as "above," "below," and the like), the health worker will likely invert the dispenser 10, so that the reservoir 13 is below the barrel 17 and the opaque body 20 surrounding it and the other electronic, electrical, and mechanical components of the dispenser 10. This "inverted" orientation is preferred for operation because it will void air trapped inside the reservoir 13 or administration line 18 during priming of the dispenser 10. The health worker next selects the desired mode, setting patient information and the dispense flow rate with the buttons 22 and display screen 23, and then starts the dispensing. Once the dispenser 10 is started, the motor 111 rotates to cycle the pump assembly 112, and the rollers 113 rotate to draw medication out of the container 12, through the tubing 77, and down and out the administration line 18. The typical flow rate range is four to twelve milliliters per hour, but the dispenser 10 is capable of operation beyond this range.

The pump assembly 112 includes an optical sensor for monitoring the rotation of the plate 115 on which the rollers 113 are mounted. This allows the printed circuit board 24 to monitor and control the dispense flow rate. Moreover, before the tubing 77 transitions to the administration line 18, downstream from the pump assembly 112, an occlusion detection apparatus (not shown) is mounted around the tubing 77; it includes a constraint around the tubing 77 which holds the tubing against a force-sensing resistor. If a force is expressed against the resistor, it will be due to a partial or full blockage somewhere downstream. The occlusion detection apparatus is electronically coupled to the printed circuit board 24, and if a blockage is detected, the dispenser 10 will produce an alarm such as a light or a sound.

A preferred embodiment is fully and clearly described above so as to enable one having skill in the art to understand, make, and use the same. Those skilled in the art will recognize that modifications may be made to the description above without departing from the spirit of the invention, and that some embodiments include only those elements and features described, or a subset thereof. To the extent that modifications do not depart from the spirit of the invention, they are intended to be included within the scope thereof.

The invention claimed is:
1. A dispenser comprising:
 a container having a reservoir, a pierceable endwall, and
  a cap fit over the container covering the endwall, the cap having an aperture disposed over the endwall and a first film covering the aperture;
a hood fit over the cap, the hood having an integral barrel defining a bore which is coaxially aligned with the aperture, a second film sealing the bore in the hood, a gasket compressed behind the second film against the hood, and a spike carried for movement in the barrel between a retracted position and an advanced position;
the first and second films are both foldable and peelable;
first and second conditions of the dispenser, wherein in the first condition the first and second films are against each other and seal the aperture and the barrel, respectively, in the second condition the first and second films are away, unsealing the aperture and the barrel, and in both the first and second conditions the cap is fit over the container and the hood is fit over the cap; and
when the dispenser is in the second condition and the spike moves from the retracted position to the advanced position, the spike extends through the gasket and pierces the endwall of the container.

2. The dispenser of claim 1, wherein the gasket compresses the first and second films against the cap.

3. The dispenser of claim 1, wherein:
the first film is adhered to the cap around the aperture; and
the second film is adhered to an inner surface of the hood around the bore.

4. The dispenser of claim 1, wherein the first and second films are each peelable films, which, when the dispenser is arranged from the first condition to the second condition, are peeled from the cap and the hood, respectively.

5. The dispenser of claim 1, wherein the first and second films are in direct contact against each other.

6. The dispenser of claim 1, wherein the hood includes an endwall, opposed clasps projecting from the endwall, and the barrel projects opposite the clasps.

7. The dispenser of claim 1, wherein in the advanced position of the spike, the spike is rotated with respect to its retracted position.

8. The dispenser of claim 1, wherein in the advanced position of the spike, the gasket makes sealing contact with the spike, the hood, and the cap.

9. The dispenser of claim 1, wherein the barrel includes a bayonet channel through which the spike moves.

10. The dispenser of claim 1, further comprising tubing coupled in fluid communication to the spike, wherein the tubing extends from the spike and through the barrel.

11. The dispenser of claim 1, wherein the reservoir contains at least one of fluorouracil, abatacept, acetominophen, acyclovir, alteplase, amikacin, amphotericin b, ampicillin, aprepitant, argatroban, aztreonam, aztreonam injection, belatacept, belimumab, bendamustine, bevacizumab, bivalirudin, bleomycin, bupivacaine, cabazitaxel, camptosar, carboplatin, carmustine, caspofungin, cefazolin, cefepime, cefmetazole, cefotetan, cefoxitin, cetuximab, chloramphenicol, cidofovir, ciprofloxacin, cisplatin, cladribine, clindamycin, cyclophosphamide, cytoxan, dacarbazine, daptomycin, daunorubicin, deferoxamine, dexmedetomidine, dexrazoxane, dobutamine, docetaxel, dopamine, doxorubicin, doxycycline, elelyso, elotuzumab, epirubicin, erbitux, ertapenem, erythromycin, etomidate, etoposide, etoposide phosphate, fentanyl, filgrastim, flagyl, fluconazole, fludarabine, fosaprepitant, foscarnet, furosemide, ganciclovir, gemcitabine, gemtuzumab ozogamicin, gentamicin, granisetron, hemin, ibritumomab tiuxetan, idarubicin, ifosfamide, imiglucerase, immune globulin, inamrinone, infliximab, intravenous immunoglobulin, ipilimumab, irinotecan, ketamine, leukine, levaquin, levobupivacaine, lidocaine, linezolid, meropenem, midazolam, mirinone, mitomycin, mitoxantrone, mylotarg, nafcillin, natalizumab, neupogen, nivolumab, norepinephrine, ofatumumab, ondansetron, oxacillin, oxalaplatin, paclitaxel, panitumumab, pertuzamab, plicamycin, polymyxin b, primaxin, propofol, quinupristin and dalfopristin, remifentanyl, rifampin, rituximab, ropivacaine, sodium valproate, streptozocin, synercid, taliglucerase alfa, teniposide, thiotepa, ticarcillin and clavulanate, tigecycline, tobramycin, topotecan, total parenteral nutrition, trastuzumab, trimetrexate, unasyn, vancomycin, vectibix, velaglucerase alfa, velcade, vinblastine, vinorelbine, vortezomib, vpriv, vumon, zoledronic acid, or zosyn.

12. A dispenser comprising:
a container having a reservoir, a pierceable endwall, and a cap fit over the container covering the endwall and having an aperture disposed over the endwall;
a hood fit over the cap, the hood having a-and integral barrel defining a bore which is coaxially aligned with the aperture;
an aseptic spiking assembly comprising:
a spike mounted for movement in the barrel;
a foldable, peelable first film applied over the cap and sealing the aperture in the cap; and
a foldable, peelable second film applied over the bore and sealing the bore in the hood with the spike behink
the aseptic spiking assembly has first and second conditions, wherein:
in the first condition of the aseptic spiking assembly, the first and second films are in contact against each other and seal the aperture and bore, respectively, and the spike is in a retracted position;
in the second condition of the aseptic spiking assembly, the first and second films are away, unsealing the aperture and the bore, and the spike is in an advanced position piercing the endwall of the container; and
in both the first and second conditions of the aseptic spiking assembly, the cap remains fit over the container and the hood remains fit over the cap.

13. The dispenser of claim 12, wherein in the advanced position of the spike, the spike is rotated with respect to its retracted position.

14. The dispenser of claim 13, wherein a gasket compresses the first and second films against the cap.

15. The dispenser of claim 14, wherein in the advanced position of the spike, the gasket makes sealing contact with the spike, the hood, and the cap.

16. The dispenser of claim 13, wherein the gasket closely receives the spike in sealing contact.

17. The dispenser of claim 12, wherein the aseptic spiking assembly further includes a gasket compressed behind the second film against the hood.

18. The dispenser of claim 12, wherein:
the first film is adhered to the cap around the aperture; and
the second film is adhered to an inner surface of the hood around the bore.

19. The dispenser of claim 12, wherein the first and second films are each peelable films, which, when the dispenser is arranged from the first condition to the second condition, are peeled from the cap and the hood, respectively.

20. The dispenser of claim 12, wherein the first and second films are in direct contact against each other.

21. The dispenser of claim 12, wherein the hood includes an endwall, opposed clasps depending from the endwall, and the barrel projects opposite the clasps.

22. The dispenser of claim 12, wherein the barrel includes a bayonet channel through which the spike moves.

23. The dispenser of claim 12, further comprising tubing coupled in fluid communication to the spike, wherein the tubing extends from the spike and through the barrel.

24. A dispenser comprising:
a container having a reservoir, a pierceable endwall, and a cap fit over the container covering the endwall, with an aperture over the endwall;
a hood fit over the cap, the hood including a-an integral barrel defining a bore which is coaxially aligned with the aperture;
an aseptic spiking assembly comprising:
a spike mounted for movement in the barrel;
a foldable, peelable first film applied to the cap; and
a foldable, peelable second film applied to the hood opposite the first film;
first and second conditions of the dispenser, wherein:
in the first condition, the first film seals the aperture, the second film seals the bore, and the spike is in a retracted position behind the second film;
in the second condition, the first film is away from the aperture, the second film is away from the bore, the aperture and bore are in open communication with each other, and the spike is moveable between the retracted and advanced positions, wherein the advanced position is defined by the spike extended through the bore, through the aperture, and through the endwall of the container to couple with the reservoir in fluid communication; and
in both the first and third conditions, the cap is fit over the container and the hood is fit over the cap.

25. The dispenser of claim 24, wherein in the advanced position, the spike is rotated with respect to its retracted position.

26. The dispenser of claim 24, wherein the aseptic spiking assembly further includes a gasket compressed behind the second film against the hood.

27. The dispenser of claim 26, wherein the gasket compressed behind the second film compresses the first and second films against the cap.

28. The dispenser of claim 26, wherein in the advanced position of the spike, the gasket makes sealing contact with the spike, the hood, and the cap.

29. The dispenser of claim 24, wherein:
the first film is adhered to the cap around the aperture; and
the second film is adhered to an inner surface of the hood around the bore.

30. The dispenser of claim 24, wherein the first and second films are each peelable films, which, when the dispenser is arranged from the first condition to the second condition, are peeled from the cap and the hood, respectively.

31. The dispenser of claim 24, wherein the first and second films are in direct contact against each other.

32. The dispenser of claim 24, wherein the hood includes an endwall, an annular sidewall projecting from the endwall, and the barrel projects opposite the annular sidewall.

33. The dispenser of claim 24, wherein the barrel includes a bayonet channel through which the spike moves.

34. The dispenser of claim 24, further comprising tubing coupled in fluid communication to the spike, wherein the tubing extends from the spike and through the barrel.

* * * * *